United States Patent [19]

Oda et al.

[11] 4,037,099

[45] July 19, 1977

[54] FLUORESCENT X-RAY SULFUR ANALYZER

[75] Inventors: Minoru Oda; Shinji Badono, both of Amagasaki, Japan

[73] Assignee: Mitsubishi Denki Kabushiki Kaisha, Tokyo, Japan

[21] Appl. No.: 631,702

[22] Filed: Nov. 13, 1975

[30] Foreign Application Priority Data

Nov. 22, 1974 Japan .................. 49-134479

[51] Int. Cl.$^2$ .......................................... G01N 23/00
[52] U.S. Cl. ............................................ 250/272
[58] Field of Search ................. 250/272, 273, 274

[56] References Cited

U.S. PATENT DOCUMENTS

| | | | |
|---|---|---|---|
| 3,076,894 | 2/1963 | Putman et al. | 250/272 |
| 3,479,506 | 11/1969 | Dorfler | 250/273 |
| 3,588,536 | 6/1971 | Dykeman | 250/274 |
| 3,766,383 | 10/1973 | Harris et al. | 250/272 |
| 3,855,470 | 12/1974 | Sahores et al. | 250/272 |

*Primary Examiner*—Alfred E. Smith
*Assistant Examiner*—B. C. Anderson
*Attorney, Agent, or Firm*—Oblon, Fisher, Spivak, McClelland & Maier

[57] ABSTRACT

A fluorescent X-ray sulfur analyzer is disclosed and includes a radiation source for irradiating a sample with X-rays or γ-rays, a radiation detector for detecting the radiation generated from the sample irradiated by the X-rays or γ-rays and a first analyzer for selecting only fluorescent X-ray pulses from the output of the detector. The analyzer further includes a first pulse rate measuring device for measuring the pulse rate of the pulses selected by the first analyzer, a second analyzer for selecting only pulses of compton scattered rays from the output of the detector and a second pulse rate measuring device for measuring the pulse rate of the pulses selected by the second analyzer. An operational circuit is provided for operating the outputs of the first and second pulse rate measuring devices and is calibrated to compensate for the error caused by the variation of the carbon-hydrogen ratio to realize an accurate weight content of the sulfur in the sample.

3 Claims, 5 Drawing Figures

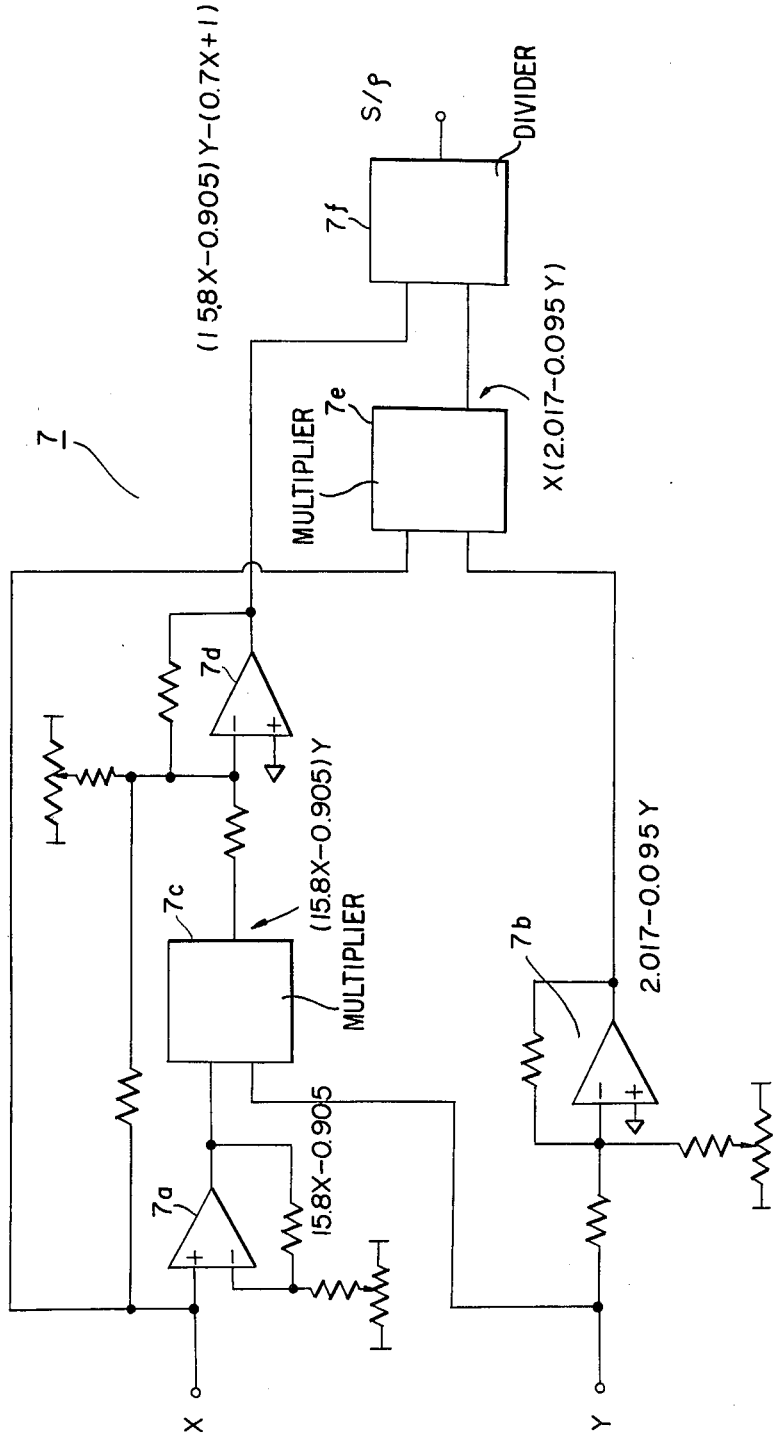
F I G. 5

FLUORESCENT X-RAY SULFUR ANALYZER

BACKGROUND OF THE INVENTION

1. Field of the Invention

The present invention relates to a fluorescent X-ray analyzer for measuring the content of sulfur in hydrocarbons. More particularly, it relates to a novel fluorescent X-ray analyzer which eliminates analytical error caused by variation of the carbon-hydrogen ratio of the sample.

2. Description of the Prior Art

Heretofore, in typical fluorescent X-ray analyzers, a sample is irradiated by $\gamma$-rays or X-rays to measure using a proportional counter fluorescent X-rays generated from sulfur in the sample to measure the weight content of the sulfur in the sample.

FIG. 1 is a block diagram of a conventional fluorescent X-ray analyzer. In FIG. 1, the reference 1 designates an X-ray dector of the energy analyzing type such as a proportional counter. However, it is possible to use a semiconductor detector, a scintillation detector, etc. as the X-ray detector.

The reference 2 designates a radiation source for irradiating the sample such as an X-ray source or a $\gamma$-ray source; 3 designates a sample; 4 designates a pulse amplifier; 5 designates a single channel pulse height analyzer; and 6 designates a scaler or a rate-meter.

The pulse signal fed from the X-ray detector 1 is amplified by the pulse amplifier 4 and only pulses resulting from fluorescent X-rays are selected by the pulse height analyzer 5. The pulse rate is measured by the scaler or the rate meter 6. The quantities analysis of sulfur is conducted by utilizing the fact that the pulse rate is substantially proportional to the weight content of sulfur.

The proportional relation between the pulse count and the sulfur content is the approximation shown in equation (1). An error is caused depending upon the variation of the carbon-hydrogen ratio of the sample of hydrocarbons.

$$\text{Pulse Rate} = \frac{KI_1 \mu_{1s} S}{(\mu_{1c} + \mu_{2c}) C + (\mu_{1h} + \mu_{2h}) H + (\mu_{1s} + \mu_{2s}) S} \quad (1)$$

wherein
C.H.S; mass of each element, C,H,S in a unit volume of the Zsample;
$\mu$; mass absorption coefficient;
suffix 1; to irradiated $\gamma$-rays;
suffix 2; to fluorescent X-rays of sulfur;
suffix $c,h,s$; to each element;
K; efficiency of the apparatus; and
$I_1$; intensity of radiation source (photon/sec)

In equation (1), the incident angle and the reflected angle to the surface of the sample are assumed to be perpendicular to the surface of the sample. In equation (1), if the absorption coefficients for C.H.S. in the denominator are equal, the denominator will be proportional to the density of the sample.

However, the absorption coefficient for H is remarkably low. Accordingly, it is not precisely proportional to the density of the sample. Therefore, the value of equation (1) does not precisely show the weight content.

The energy of the irradiated X-rays and the energy of fluorescent X-rays of sulfur are respectively given as 8 and 2.3 KeV and, when substituted in equation (1), yield equation (1)'.

$$\text{Pulse Rate} = \frac{KI_1 80 S}{185C + 3H + 300S}$$
$$= 0.43 \, KI_1 \frac{S}{C + 0.017H + 1.75S} \quad (1)'$$

The weight content of hydrogen in hydrocarbons is usually in the range of 8 –15% wt. Accordingly, the value of equation (1)' deviates about 6% wt. from the true value according to the variation of the carbon-hydrogen ratio. Thus, as stated above, in a conventional fluorescent X-ray analyzer, the error caused by the variation of the carbon-hydrogen ratio of the sample is detected but the error is not easily correctable.

SUMMARY OF THE INVENTION

It is an object of the present invention to provide a fluorescent X-ray sulfur analyzer in which the error caused by the conventional analyzer is eliminated by utilizing compton scattered rays.

The foregoing and other objects are attained in accordance with one aspect of the present invention through the provision of a fluorescent X-ray sulfur analyzer which comprises a radiation source for irradiating a sample with X-rays or $\gamma$-rays; a radiation detector of the energy analyzing type such as a proportional counter for detecting the radiation generated from the sample irradiated by the X-ray or $\gamma$-rays; a first analyzer such as a single channel pulse height analyzer for selecting only fluorescent X-ray pulses from the output of the detector; a first pulse rate measuring device comprising a scaler or a rate meter for measuring the pulse rate of the pulses selected by the first analyzer; a second analyzer such as a single channel pulse height analyzer for selecting only pulses of compton scattered rays from the output of the detector; a second pulse rate measuring device comprising a scaler or a rate meter for measuring the pulse rate of the pulses selected by the second analyzer; and an operational circuit for quantitative analysis of the sulfur in hydrocarbons utilizing the outputs X and Y of the first and second pulse rate measuring devices in the following equation $$\frac{S}{\rho} = \frac{X(2.017 - 0.095Y)}{(15.8X + 0.905)Y - (0.7X - 1)}$$

so that the error caused by the carbon-hydrogen ratio is calibrated to yield a precise weight content of sulfur.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 5 is a circuit diagram of one embodiment of the operational circuit 7 in FIG. 2.

DETAILED DESCRIPTION OF THE PREFERRED EMBODIMENTS

Figure 1:
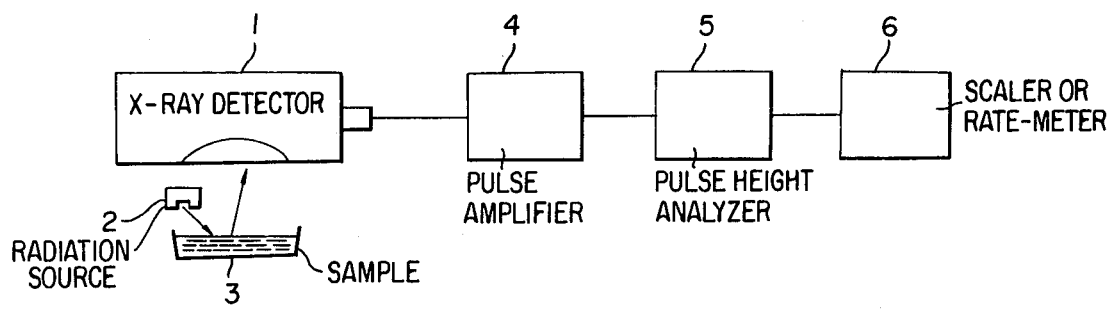
FIG. 1 is a block diagram of a conventional fluorescent X-ray analyzer.

Referring now to the drawings, wherein like reference numerals designate identical or corresponding parts throughout the several views, one embodiment of the fluorescent X-ray analyzer will be described.

Figure 2:
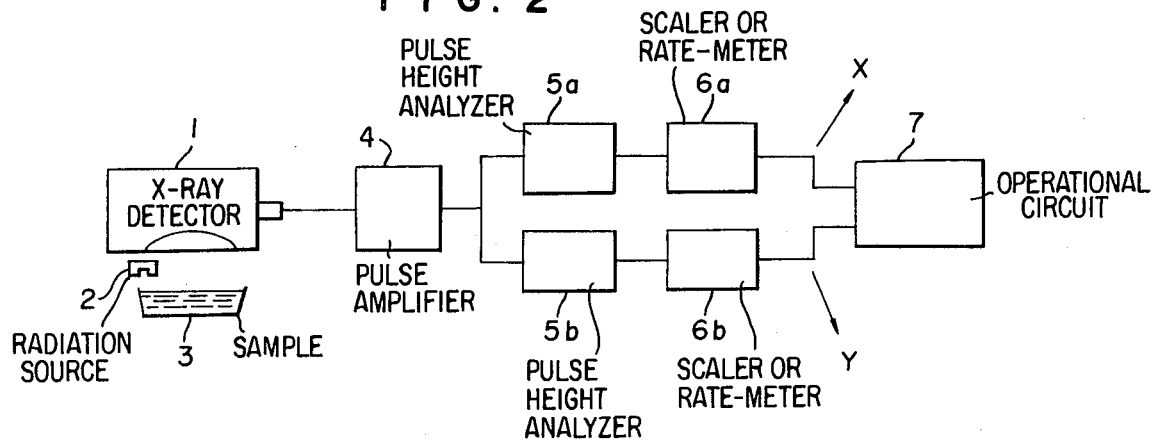
FIG. 2 is a block diagram of one embodiment of the fluorescent X-ray analyzer according to the present invention.

In FIG. 2, the reference 1 designates an X-ray detector which is the same as that of FIG. 1; 2 designates a radiation source which is the same as that of FIG. 1; 3 designates a sample; 4 designates a pulse amplifier; 5a and 5b designate single channel pulse height analyzers; 6a and 6b designate scalers or rate meters; and 7 designates an analogue or digital operational circuit.

The function of the single channel pulse height analyzer 5a and the scaler or the rate meter 6a is to measure the pulse rates of the fluorescent X-ray pulses as is done in the apparatus of FIG. 1. The analyzer of the invention includes the single channel pulse height analyzer 5b and the scaler or the rate meter 6b to select compton scattered rays and to perform a count with respect thereto.

The principle for calibrating the error caused by the carbon-hydrogen ratio by utilizing the compton scattered rays in the analyzer will now be described. The compton scattered rays reach the detector after overcoming self-absorption in the sample after the irradiated X-rays or γ-rays are scattered in the sample in the fluorescent X-ray analysis. In conventional measurements, the compton scattered rays have been considered to be an undesirable background signal.

When the procedure for generating the compton scattered rays is considered, it is realized that the hydrogen atom has about two times the comtpon scattering power per mass compared to the other elements and has a lower total mass absorption coefficient for determining self-absorption for X-rays having less than 20 KeV of energy compared to the other elements (C and S). Therefore, the generation of compton scattered rays is increased if there is an increase in the content of hydrogen. It is possible to measure the carbon-hydrogen ratio of the sample by utilizing this fact.

The relation between the intensity of the compton scattered rays and the elements ratio of the sample is given by the equation (2).

$$I = I_1 K \int_0^\infty e^{-(\mu_{1c}C + \mu_{1h}H + \mu_{1s}S)x} \cdot (\mu'_{1c}C + \mu'_{1h}H + \mu'_{1s}S) \cdot e^{-(\mu''_{1c}C + \mu''_{1h}H + \mu''_{1s}S)x} dx$$

wherein
I; intensity of compton scattered rays;
$\mu'$; compton scattering coefficient for irradiated X-rays;
$\mu''$; mass absorption coefficient for compton scattered rays.

The energy of the detected compton scattered rays is substantially the same as that of the irradiated X-rays (slightly lower in practical operation). Accordingly, $\mu''$ is substantially the same as $\mu$. When the approximation $\mu'' = \mu$ is considered, equation (2) is modified as follows.

$$I = \frac{KI_1}{2} \cdot \frac{\mu'_{1c}C + \mu'_{1h}H + \mu'_{1s}S}{\mu_{1c}C + \mu_{1h}H + \mu_{1s}S} \quad (2)'$$

$$= \frac{KI_1}{2} \cdot \frac{0.2C + 0.4H + 0.2S}{4.6C + 0.5H + 80S}$$

$$= 0.028 KI_1 \frac{C + 2H + S}{C + 0.11H + 17.4S}$$

Figure 3:
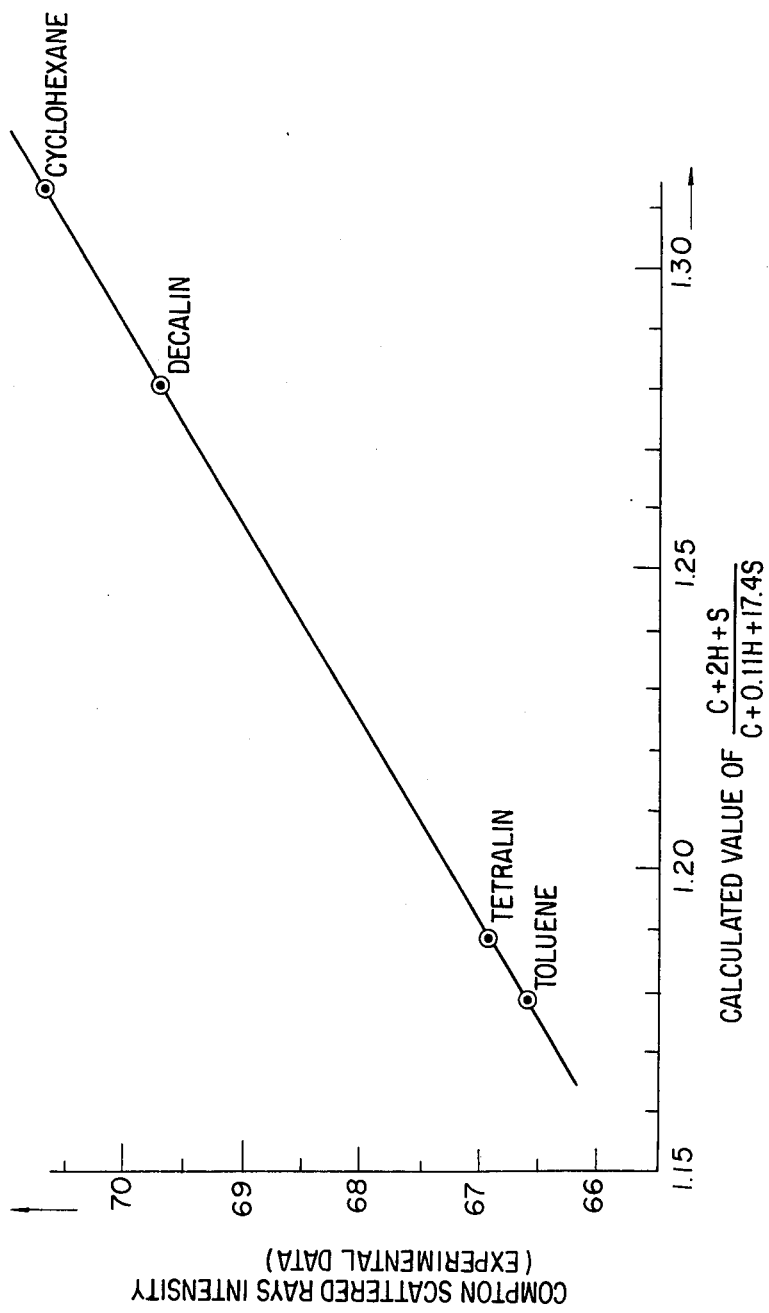
FIG. 3 is an experimental data graph showing the principle of the invention.
Figure 4:
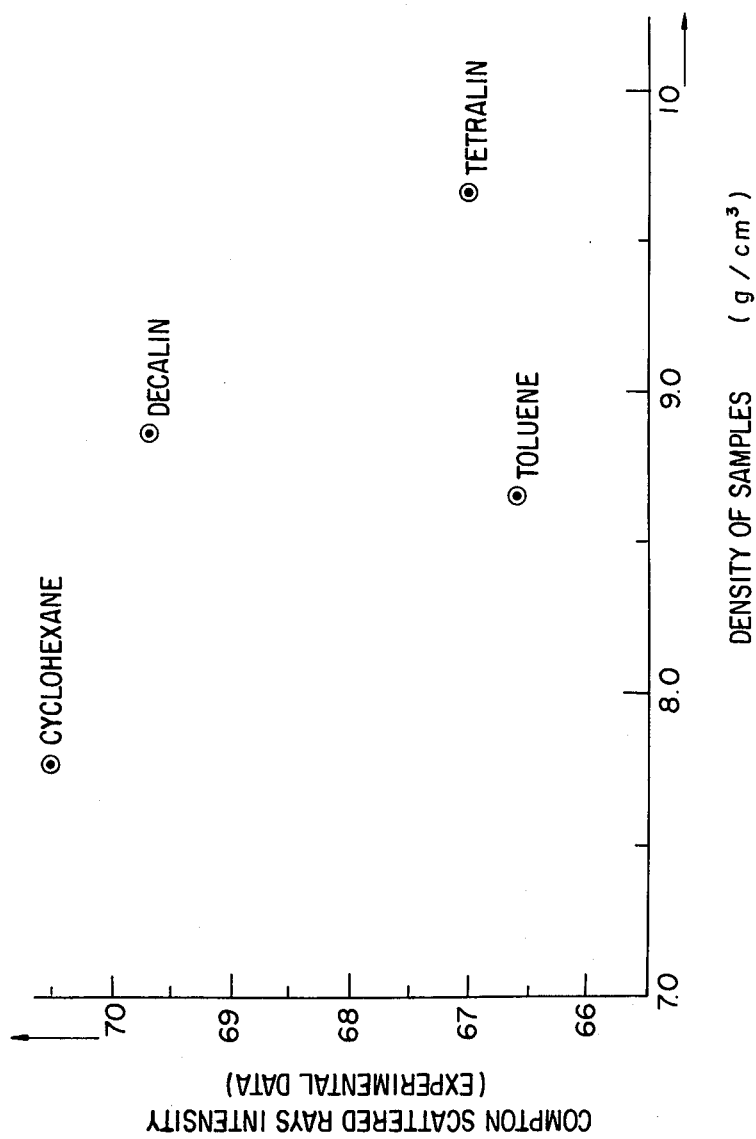
FIG. 4 is a reference data graph showing the principle of the invention.

In order to confirm the applicability of equation (2)', tests were conducted on four samples which have different carbon-hydrogen ratios and different densities. The results are shown in FIG. 3. The compton scattered rays intensity was measured by a measuring device with specific characteristics constants corresponding to c.p.s. (counts per second). The measured values are shown in the ordinate. The calculated values of (C + 2H + S/C + 0.11H + 17.4S) are shown in the abscissa. As a reference, the relation of the intensities of compton scattered rays to the densities of the samples is shown in FIG. 4.

It is clear that the intensity of the compton scattered rays is not dependent upon the density of the sample, but, rather is, dependent upon the ratio of the elements of the sample. This means that the error caused by the carbon-hydrogen ratio of the sample can be eliminated by appropriate compensation in operational circuit 7.

The operational equation required for operational circuit 7 should have sufficient calibration accuracy to prevent economic loss of the analyzer. The solution to this problem is not always readily apparent.

One example for satisfying the above-mentioned requirements will now be described. The equations (1)', (2)' are modified as follows.

Equation (1)':

$$0.43 KI_1 \frac{S}{C + 0.017H + 1.7S} \quad (1)''$$

$$= 0.43 KI_1 \frac{S}{\rho - 0.983H + 0.7S} = 0.43 KI_1 X$$

Equation (2)':

$$0.028 KI_1 \frac{C + 2H + S}{C + 0.11H + 17.4S} \quad (2)''$$

$$= \frac{\rho + H}{\rho - 0.89H + 16.4S} = 0.028 KI_1 Y$$

wherein $\rho = C + H + S$, density.

The term H is eliminated from the equations (1)" and (2)" and the solution of the equations when the energy of the irradiated X-ray is 8 KeV is as follows.

$$\frac{S}{\rho} = \frac{X(2.017 - 0.095Y)}{(15.8X + 0.905)Y - (0.7X - 1)} \quad (3)$$

FIG. 5 shows one embodiment of operational circuit 7 for attaining the operation equation (3).

In FIG. 5, the references 7c and 7e designate multipliers; 7f designates a divider and 7a, 7b and 7d designate differential amplifiers. The invention is not so limited and various equivalents can be utilized.

When the economic advantage of the analyzer is considered, equation (3) can be degenerated. Accordingly, the structure of FIG. 5 is satisfactory for attaining the purpose of this invention.

It is possible to superpose each signal caused by background counts to the signal X and the signal Y. This can be eliminated by modifying equation (3) subtracting background signals from X and Y.

As is clear from the above-mentioned illustration, in accordance with the fluorescent X-ray sulfur analyzer of the invention, the error caused by the variations of the carbon-hydrogen ratio can be calibrated although the error is not eliminated by a conventional analyzer. The calibration of the error can be attained by adding only an electronic circuit and does not necessitate the addition of a separate radiation detector. Accordingly, it is quite economical.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by letters patent of the United States is:

1. A fluorescent X-ray sulfur analyzer comprising:
   a radiation source for irradiating a sulfur containing hydrocarbon sample with X-rays or γ-rays,
   a radiation detector for detecting the radiation generated from the sulfur containing hydrocarbon sample irradiated by the X-rays or γ-rays,
   a first analyzer connected to the output of the radiation detector for selecting only fluorescent X-ray pulses from the output of the radiation detector,
   a first pulse rate measuring device connected to the output of the first analyzer for measuring the pulse rate of the pulses selected by the first analyzer,
   a second analyzer connected to the output of the radiation detector for selecting only pulses of compton scattered rays from the output of the radiation detector,
   a second pulse rate measuring device connected to the output of the second analyzer for measuring the pulse rate of the pulses selected by the second analyzer, and
   an operational circuit connected to the output of the first pulse rate measuring device and connected to the output of the second pulse rate measuring device for compensating for the error caused by the variation of the carbon-hydrogen ratio to realize an accurate weight content of the sulfur in the sulfur containing hydrocarbon sample by performing the function $$\frac{S}{\rho} = \frac{X(2.017 - 0.095Y)}{(15.8X + 0.905)Y - (0.7X - 1)}$$

wherein $S/\rho$ is the sulfur mass per unit weight of the sulfur containing hydrocarbon sample, X is the output signal of the first pulse rate measuring device and Y is the output signal of the second pulse rate measuring device.

2. The fluorescent X-ray sulfur analyzer according to claim 1 wherein the first analyzer and the second analyzer each comprise a single channel pulse height analyzer.

3. The fluorescent X-ray sulfur analyzer according to claim 1 wherein the first pulse rate measuring device and the second pulse rate measuring device each comprise a scaler or a rate meter.

* * * * *